United States Patent [19]

Hodge

[11] Patent Number: 4,516,438
[45] Date of Patent: May 14, 1985

[54] STANDARDIZED SAMPLING HAY PROBE

[76] Inventor: Allan M. Hodge, 5852 Lomond Dr., San Diego, Calif. 92120

[21] Appl. No.: 534,079

[22] Filed: Sep. 20, 1983

[51] Int. Cl.³ .............................................. G01N 1/08
[52] U.S. Cl. .................................................. 73/864.44
[58] Field of Search ........... 73/864.41, 864.44, 864.45, 73/864.51; 175/58, 405

[56] References Cited

U.S. PATENT DOCUMENTS

| 3,016,749 | 1/1962 | Wollner | 73/864.45 |
| 3,064,482 | 11/1962 | Wollner | 73/864.45 |
| 3,921,459 | 11/1975 | Willett | 73/864.41 |

FOREIGN PATENT DOCUMENTS 1119412  7/1968  United Kingdom ............. 73/864.41

Primary Examiner—S. Clement Swisher
Attorney, Agent, or Firm—Poms, Smith, Lande & Rose

[57] ABSTRACT

A hay probe for taking samples from bales of hay includes a pair of heavy duty handles, a central mounting assembly, and an elongated probe, in the order of about a foot in length, and having an inner diameter in the order of about ⅜ths of an inch. Attached to the mounting assembly opposite to the probe tube is an impermeable sampling container such as a Mason jar. An elongated tamping rod is provided for pushing the contents of the probe tube into the container. Standardized samples may be obtained using, for example, 15 samples, which will substantially fill a normal one pint Mason jar.

19 Claims, 5 Drawing Figures

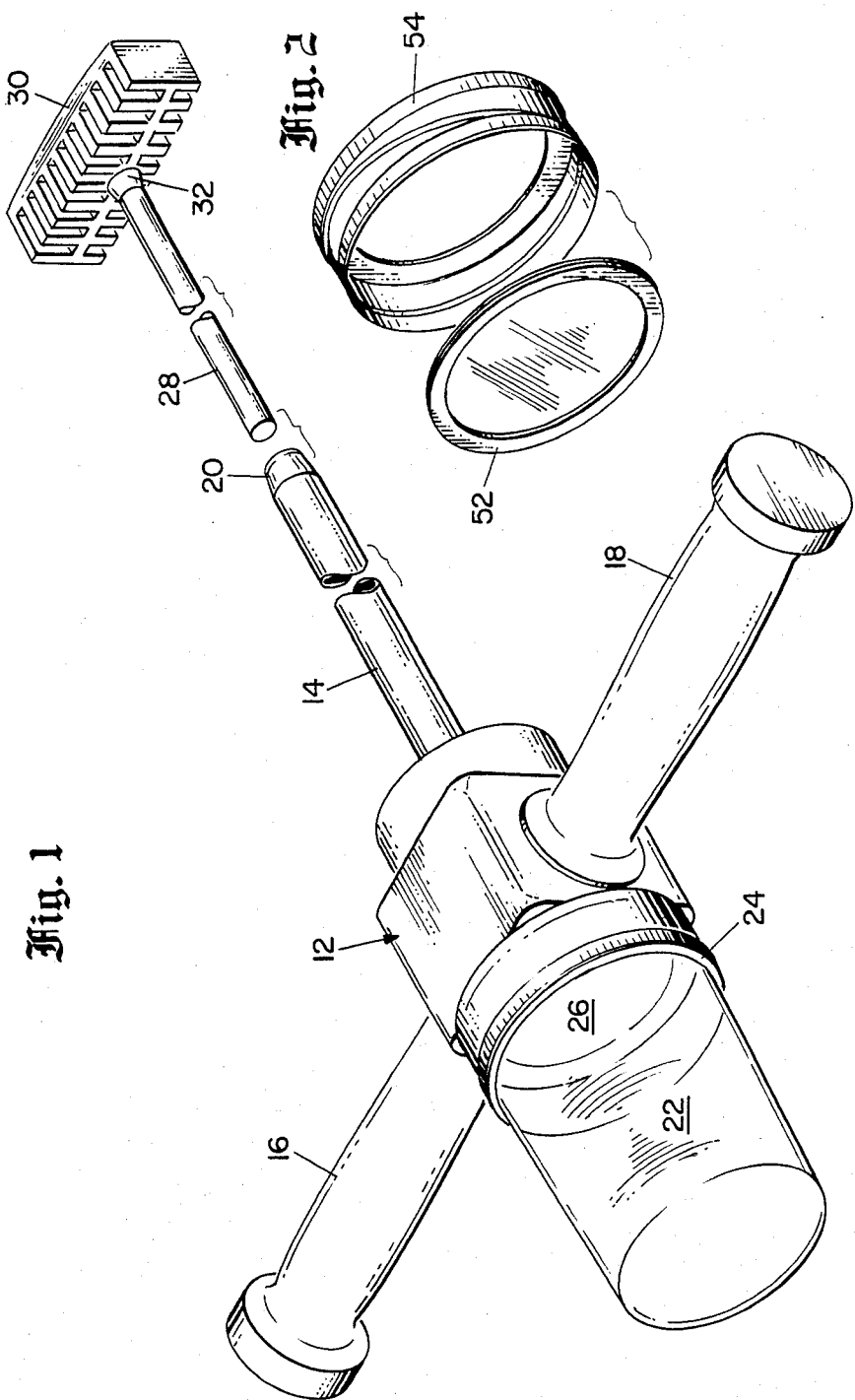

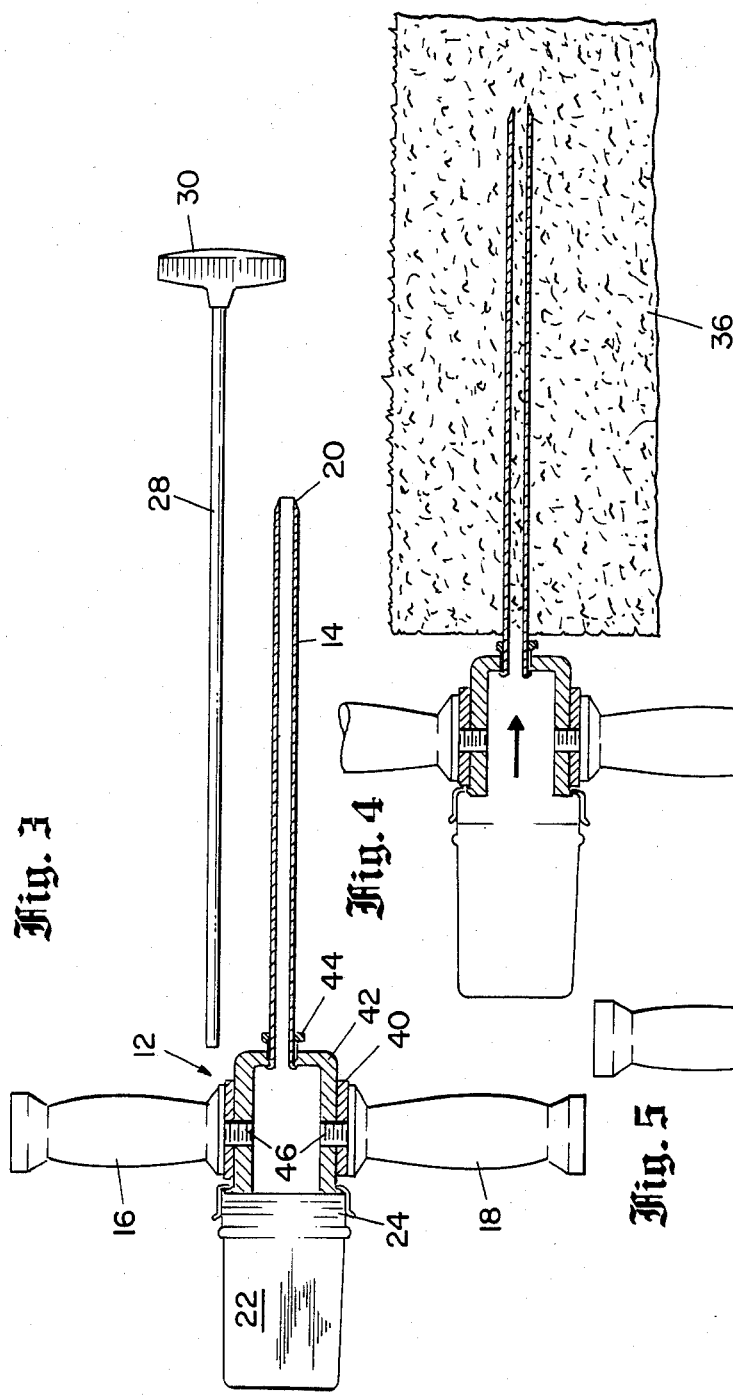

STANDARDIZED SAMPLING HAY PROBE

FIELD OF THE INVENTION

This invention relates to probe assemblies for collecting samples of hay or the like for purposes of analysis.

BACKGROUND OF THE INVENTION

When large quantities of hay are to be purchased, for cattle feed or the like, it is desirable to sample the bales of hay and determine the content of certain key ingredients including (1) moisture content, (2) protein content, (3) fiber content, and (4) content of lignin. In this regard, for example, a moisture or water content of 12 to 15% would be considered acceptable, while more than 18% would be undesirable, as the hay would be likely to mildew or otherwise spoil, because it had not been adequately cured or had been subject to excessive moisture prior to bailing. Also, for example, a level of protein in the order of 21%, would be desirable; but the availability to the cattle also depends on the amount of lignin present in the hay, as high levels of lignin indicate that the protein may be encapsulated by the lignin and thus may not be available for digestion and utilization by the cattle. In this regard, for example, a lower level of lignin in the order of 4 or 5% would be acceptable, while a higher level such as $7\frac{1}{2}$ or 8% might be so high that much of the otherwise available protein would not be available for utilization by the cattle.

Incidentally, the most common method employed for analyzing a hay sample is chemical; however, a near infrared reflectance analyzer may be used and these are available from a number of manufacturers including Technicon of New York.

In accordance with practices which have been employed heretofore, the hay probe units which have been used frequently have a relatively long tube, such as 2 or 3 feet in length, and a relatively large diameter, such as one inch. Also, relative small constant diameter tubes, in the order of one-quarter inch in diameter have been used. In addition, the samples have customarily been held in an inexpensive air permeable plastic bag or a paper bag, and delivered to a laboratory for analysis up to several days later. Also, because the amount of hay in the sample, as contained in the paper bag or the plastic bag, may vary substantially, the laboratory may have difficulty in selecting the volume of material necessary for analysis in a manner which will keep it representative of the whole sample. Likewise, the necessary preliminary grinding step may be very quick if the sample was taken with a small diameter probe because the fibers in the material have been cut to a short length. Conversely, if the sample was taken with a large diameter probe, the grinding step may take a proportionately longer time, even possibly to the extent of having to be done twice. Unfortunately, this has the effect of subjecting the hay to the ambient humidity conditions and the final measured moisture content may be significantly different from that which is actually present in the baled hay. In addition, when large diameter probes are employed, different amounts of hay are obtained from soft bales of hay than from hard packed bales of hay, because different levels of penetration of the probe occur. This varies the amount of material which is taken from each bale, and thus varies the resultant analysis. Also, sheets of paper are often included within the sample bags for identification purposes, and this will tend to alter the analysis, as the paper may absorb moisture from the sample.

From the foregoing description, it is evident that the prior techniques have left much to be desired, and the analysis results have related to the sample as ultimately tested in the laboratory, which often has had only a remote relationship to the material actually present in the bales of hay supposedly being tested. Accordingly, it is a principal object of the invention to provide a hay probe assembly and technique for obtaining standardized samples which will more accurately reflect the actual content of the hay being sampled than arrangements which have been used heretofore.

SUMMARY OF THE INVENTION

In accordance with one aspect of the present invention, a hay probe apparatus includes a central mounting assembly to which are secured handle arrangements, and from which central assembly a hollow sharpened hay probe tube extends in one direction, with the hay probe communicating with an impermeable container of a standardized volume for holding a predetermined number of probe samples.

Additional features of the invention include (1) the use of a tamper element for pushing the hay sample into the impermeable container, with the tamper having a handle with an extension facing the hay probe to protect the fingers of the user against the sharp edges at the end of the probe; (2) the use of a hay probe having a relatively short length, in the order of 8 to 16 inches, preferably about one foot; and a relatively small inner diameter in the order of $\frac{1}{4}$ to $\frac{5}{8}$ of an inch, preferably about one-half inch, in order to obtain full depth standard samples on each use of the probe; (3) the provision of a slightly smaller diameter at the cutting edges of the probe so that the sample will pass through the probe length more easily; (4) the use of a pair of heavy duty handles extending transverse to the probe tube; and (5) forming the hay probe tue of stainless steel.

Other objects, features and advantages of the invention will become apparent from a consideration of the following detailed description and from the accompanying drawings.

BRIEF DESCRIPTION OF THE DRAWINGS

FIG. 1 is an overall assembly view of a hay probe and tamper unit illustrating the principles of the invention;

FIG. 2 shows a Mason type jar top and screw cap for securing to the sample jar when it is removed from the hay probe;

FIG. 3 shows a transverse cross-sectional view of the hay probe assembly and the tamper unit;

FIG. 4 shows the taking of a sample from a bale of hay; and

FIG. 5 illustrates the use of the tamper rod in ejecting the collected sample into the impermeable sample collecting jar.

DETAILED DESCRIPTION

Referring more particularly to the drawings, FIG. 1 shows a central mounting assembly 12 to which a hay probe tube 14 is secured, and a pair of transversely extending handles 16 and 18 which are also firmly secured to the mounting assembly 12. The probe tube 14 may be formed of stainless steel and may be approximately one foot in length. It may have an inner diameter of approximately $\frac{1}{2}$ inch and an outer diameter of approximately $\frac{5}{8}$ inch, with its outer end 20 being sharpened by grinding toward the inner diameter of the tube. In addition, the front end of the probe is rolled down to a slightly smaller diameter, such as 7/16 inch, to reduce friction as the sample passes through the probe. Secured to the mounting assembly 12 is a Mason jar 22 forming an impermeable container for receiving samples of hay from the probe tube 14. The Mason jar 22 may be secured to the assembly 12 by a standard screw-type top 24 which has an open center 26 and which is firmly attached to the mounting assembly 12.

A rod-like tamper member 28 is provided with a handle 30 which includes an extension 32 which abuts the sharp edge of the probe tube 14 adjacent its sharpened edge 20 so that the fingers of the user are not cut, when the tamper rod 28 is used to push the hay sample in tube 14 into the impermeable container 22.

The steps in taking a sample are shown in FIGS. 3, 4 and 5. Initially, the probe rod 28 is removed from the probe tube 14, and the probe is inserted into a bale of hay 36 as indicated in FIG. 4. Following removal from the bale of hay, the tamper rod 28 is forced into the probe tube and ejects the sample of hay 38 into the impermeable container 22. The function of the raised central portion 32 on the handle 30, is particularly evident from a consideration of FIG. 5. The member 32 will engage the sharp end 20 of the probe tube 14, and thus prevent the fingers of the user from being cut.

Concerning the construction of the assembly, the handles 16 and 18 may be made of heavy-duty, high-strength plastic and may be in the order of 5 or 6 inches in length. They may have a roughened exterior surface for ease in gripping. The diameter of the ends of the handles are about 1½ inches and the gripping portion are approximately 1¼ in diameter to provide a solid and firm gripping surface. The central mounting assembly may be formed of an outer rectangular or square steel or aluminum member 40 and an inner bell-shaped member 42. The stainless steel probe tube 14 is secured into the bell-shaped member 42 by the threaded pipe-type fitting 44. The handles 16 and 18 are provided with threaded bolt-like extensions 46, and these make threaded engagement with tapped holes in the bell-shaped tube member 42. In general, the central mounting assembly 12 is of heavy-duty rugged construction to stand the heavy usage to be expected of a tool of this type.

Incidentally, FIG. 2 shows, for completeness, a Mason jar lid 52 and a screw-top 54 which are employed to seal the sample which is collected in the impermeable Mason jar sample container 22.

It has been determined that a pint jar will receive 15 samples from the ⅜ inch inner diameter probe tube 14, and that similarly, a quart jar will receive 30 samples, and a half pint jar 7 or 8 samples. Using a pint jar, and recognizing that 15 samples are to be taken, when a lot of baled hay is to be purchased, the total number of bales is counted, and this number of bales of hay is divided by 15. Thus, for example, if there were 300 bales of had in a lot for which purchase is considered, 300 would be divided by 15, with the result that every 20th bale of hay is sampled. This provides exactly 15 samples, and produces a standardized completely full pint jar of hay to be analyzed. This sample is then taken to the laboratory or to the analyzing equipment owned by the dairy farmer, it is run through a standardized grinding operation, and is then analyzed for the content of at least the four major components mentioned hereinabove, i.e., (1) moisture, (2) protein, (3) fiber, and (4) lignin. Further, it is not necessary to place identifying pieces of paper inside the jar, as they may reduce or add to the moisture of the contents, as identifying labels may be affixed to the exterior of the jar. When these precautions are followed, the analysis will closely reflect the actual composition of the baled hay which as been sampled.

It is to be understood that the foregoing description and the accompanying drawings illustrate the principles of the invention. However, it is also to be understood that various changes and alternative construction may be employed without departing from the spirit and scope of the present invention. By way of example, and not of limitation, the standardized probe may have slightly different dimensions than that described hereinabove, and the central mounting assembly could be made in a different configuration, while retaining its ruggedness. Also, instead of using a Mason jar, other impermeable containers could be used. Accordingly, the present invention is not limited to that precisely as shown and described hereinabove.

What is claimed is:

1. A hay probe apparatus for obtaining standardized samples of hay for analysis of the actual contents of bales of hay or similar material, comprising:

an elongated hollow metal probe tube, having an inner diameter in the order of one-quarter to five-eighths inch, and a length in the order of eight to sixteen inches, said tube being sharpened at one end;

central mounting assembly secured to the other end of said probe tube;

a pair of handles mounted to said central mounting assembly transverse to said probe;

impermeable container means removably secured to said mounting assembly for receiving hay samples from said probe tube and for maintaining them in substantially the same condition as when the samples were taken from bales of hay; and tamper rod means for transferring hay samples from said probe tube to said impermeable container;

whereby the samples of a standard volume may be analyzed without significant changes in moisture content or the like between sampling and testing.

2. A hay probe apparatus as defined in claim 1 wherein said impermeable container means is a pint jar of the Mason jar type.

3. A hay probe apparatus as defined in claim 1 wherein handle means are provided for said tamper including an extension adjacent the rod for preventing contact between the users fingers and the sharpened end of said probe tube.

4. A hay probe apparatus as defined in claim 1 wherein said probe tube has its outer end sharpened in a taper extending from the outer diameter of said tube outward to the inner diameter of the tube.

5. A hay probe apparatus as defined in claim 1 wherein said impermeable container has a threaded open end, and wherein mating threaded holding means are secured to said mounting assembly.

6. A hay probe apparatus as defined in claim 1 wherein said probe tube has an inner diameter of approximately ½ inch, and said probe tube is about one foot long.

7. A hay probe as defined in claim 1 wherein the diameter of the hay probe tube at the cutting edge is slightly less than the diameter of the remainder of the hay probe tube.

8. A hay probe as defined in claim 1 wherein said hay probe tube is formed of stainless steel.

9. A hay probe apparatus for obtaining standardized samples of hay for analysis of the actual contents of bales of hay or similar material, comprising:
    an elongated hollow metal probe tube, said tube being sharpened at one end;
    a central mounting assembly secured to the other end of said probe tube;
    handle means mounted to said central mounting assembly and extending outwardly transverse to said probe;
    impermeable container means removably secured to said mounting assembly for receiving hay samples from said probe tube and for maintaining them in substantially the same condition as when the samples were taken from bales of hay; and
    tamper rod means for transferring hay samples from said probe tube to said impermeable container;
    whereby the samples of a standard volume may be analyzed without significant changes in moisture content or the like between sampling and testing.

10. A hay probe apparatus as defined in claim 9 further comprising tamper rod means for transferring hay samples from said probe tube to said impermeable container.

11. A hay probe apparatus as defined in claim 9 wherein handle means are provided for said tamper including an extension adjacent the rod for preventing contact between the users fingers and the sharpened end of said probe tube.

12. A hay probe apparatus as defined in claim 9 wherein said probe tube has its outer end sharpened in a taper extending from the outer diameter of said tube outward to the inner diameter of the tube.

13. A hay probe apparatus as defined in claim 9 wherein said impermeable container has a threaded open end, and wherein mating threaded holding means are secured to said mounting assembly.

14. A hay probe apparatus as defined in claim 9 wherein said probe tube has an inner diameter of approximately ⅜ inch, and said probe tube is about one foot long.

15. A hay probe as defined in claim 9 wherein the diameter of the hay probe tube at the cutting edge is slightly less than the diameter of the remainder of the hay probe tube.

16. A hay probe as defined in claim 9 wherein said hay probe tube is formed of stainless steel.

17. A hay probe apparatus for obtaining standardized samples of hay for analysis of the actual contents of bales of hay or similar material, comprising:
    an elongated hollow metal probe tube, said tube being sharpened at one end;
    a central mounting assembly secured to the other end of said probe tube;
    handle means mounted to said central mounting assembly and extending outwardly transverse to said probe;
    impermeable container means removably secured to said mounting assembly for receiving hay samples from said probe tube and for maintaining them in substantially the same condition as when the samples were taken from bales of hay;
    tamper rod means for transferring hay samples from said probe tube to said impermeable container; and
    handle means for said tamper including an extension adjacent the rod for preventing contact between the users fingers and the sharpened end of said probe tube;
    whereby the samples of a standard volume of hay may be analyzed without significant changes in moisture content or the like between sampling and testing.

18. A hay probe apparatus as defined in claim 1 wherein said hay probe tube is of constant inner diameter.

19. A hay probe apparatus as defined in claim 9 wherein said hay probe tube is of constant inner diameter.

* * * * *